US010786229B2

(12) United States Patent
McBean et al.

(10) Patent No.: US 10,786,229 B2
(45) Date of Patent: Sep. 29, 2020

(54) DIAGNOSTIC DEVICES AND METHODS FOR MITIGATING HOOK EFFECT AND USE THEREOF

(71) Applicant: Ellume Limited, Queensland (AU)

(72) Inventors: Rhiannon McBean, Queensland (AU); Scott Fry, Queensland (AU); Sean Parsons, Queensland (AU)

(73) Assignee: Ellume Limited, Queensland (AU)

( * ) Notice: Subject to any disclaimer, the term of this patent is extended or adjusted under 35 U.S.C. 154(b) by 596 days.

(21) Appl. No.: 15/544,232

(22) PCT Filed: Jan. 22, 2016

(86) PCT No.: PCT/AU2016/050037
§ 371 (c)(1),
(2) Date: Jul. 17, 2017

(87) PCT Pub. No.: WO2016/115608
PCT Pub. Date: Jul. 28, 2016

(65) Prior Publication Data
US 2018/0008239 A1    Jan. 11, 2018

(30) Foreign Application Priority Data
Jan. 22, 2015    (AU) .................. 2015900186

(51) Int. Cl.
*A61B 10/00*    (2006.01)
*G01N 33/543*    (2006.01)
(Continued)

(52) U.S. Cl.
CPC ........ *A61B 10/0012* (2013.01); *A61B 5/1468* (2013.01); *A61B 5/14546* (2013.01);
(Continued)

(58) Field of Classification Search
CPC .............. A61B 10/0012; A61B 10/007; A61B 5/14546; A61B 5/1468; A61B 5/4343;
(Continued)

(56) References Cited
U.S. PATENT DOCUMENTS

| 4,338,305 A | 7/1982 | Corbin |
| 4,999,287 A | 3/1991 | Allen et al. |

(Continued)

FOREIGN PATENT DOCUMENTS

| CA | 2496986 | 10/2005 |
| CA | 2802318 | 1/2012 |

(Continued)

OTHER PUBLICATIONS

Adejuwon et al. (1984) "Daily serum choriogonadotropin concentrations in early human gestation"; Int J Gynaecol Obstet. 22(2); pp. 125-129.

(Continued)

*Primary Examiner* — Eric F Winakur
*Assistant Examiner* — Abid A Mustansir
(74) *Attorney, Agent, or Firm* — Carol L. Francis; Bozicevic, Field & Francis LLP

(57) ABSTRACT

The present disclosure relates to devices and methods for identifying conditions in a human or animal body, such as pregnancy or ovulation. For example, the present disclosure relates to devices and methods for identifying pregnancy or ovulation, which devices and methods are adapted to mitigate the "hook effect", thereby improving accuracy of the devices and methods.

17 Claims, 6 Drawing Sheets

(51) Int. Cl.
   *G01N 33/76* (2006.01)
   *G01N 33/558* (2006.01)
   *G01N 33/68* (2006.01)
   *A61B 5/145* (2006.01)
   *A61B 5/1468* (2006.01)
   *A61B 5/00* (2006.01)

(52) U.S. Cl.
   CPC ............ *A61B 5/4343* (2013.01); *A61B 5/742* (2013.01); *A61B 10/007* (2013.01); *G01N 33/54386* (2013.01); *G01N 33/558* (2013.01); *G01N 33/689* (2013.01); *G01N 33/76* (2013.01); *A61B 2562/0295* (2013.01); *G01N 2333/59* (2013.01)

(58) Field of Classification Search
   CPC ............ A61B 5/742; A61B 2562/0295; G01N 33/558; G01N 33/689; G01N 33/54386; G01N 33/76; G01N 2333/59
   See application file for complete search history.

(56) References Cited

U.S. PATENT DOCUMENTS

| | | | |
|---|---|---|---|
| 5,418,136 A | 5/1995 | Miller et al. | |
| 5,503,985 A | 4/1996 | Cathey et al. | |
| 5,525,520 A | 6/1996 | Dinh | |
| 5,629,214 A | 5/1997 | Crosby | |
| 5,783,399 A | 7/1998 | Childs et al. | |
| 5,786,220 A | 7/1998 | Pronovost et al. | |
| 5,824,268 A | 10/1998 | Bernstein et al. | |
| 5,902,982 A | 5/1999 | Lappe | |
| 5,939,252 A | 8/1999 | Lennon et al. | |
| 5,942,407 A | 8/1999 | Liotta et al. | |
| 5,998,220 A | 12/1999 | Chandler | |
| 6,033,627 A | 3/2000 | Sheilds et al. | |
| 6,136,610 A * | 10/2000 | Polito .............. G01N 33/54386 422/82.05 | |
| 6,248,294 B1 | 6/2001 | Nason | |
| 6,267,722 B1 | 7/2001 | Anderson et al. | |
| 6,319,665 B1 | 11/2001 | Zwanziger et al. | |
| 6,319,965 B1 | 11/2001 | Kamohara et al. | |
| 6,352,862 B1 * | 3/2002 | Davis .............. G01N 33/54386 422/402 | |
| 6,365,417 B1 | 4/2002 | Fleming et al. | |
| 6,454,705 B1 | 9/2002 | Cosentino et al. | |
| 6,549,275 B1 | 4/2003 | Cabuz et al. | |
| 6,627,459 B1 | 9/2003 | Tung et al. | |
| 6,656,745 B1 | 12/2003 | Cole | |
| 6,764,849 B2 | 7/2004 | Small et al. | |
| 6,886,864 B2 | 5/2005 | Nelson et al. | |
| 6,991,940 B2 | 1/2006 | Carroll et al. | |
| 6,998,273 B1 | 2/2006 | Fleming et al. | |
| 7,044,919 B1 | 5/2006 | Catt et al. | |
| 7,070,920 B2 | 7/2006 | Spivey et al. | |
| 7,214,542 B2 | 5/2007 | Hutchinson | |
| 7,220,597 B2 | 5/2007 | Zin et al. | |
| 7,279,136 B2 | 10/2007 | Takeuchi et al. | |
| 7,280,201 B2 | 10/2007 | Helbing | |
| 7,300,800 B2 | 11/2007 | Bell et al. | |
| 7,315,378 B2 | 1/2008 | Phelan et al. | |
| 7,459,314 B2 | 12/2008 | Guo et al. | |
| 7,460,222 B2 | 12/2008 | Kalveram et al. | |
| 7,486,396 B2 | 2/2009 | Oldham et al. | |
| 7,488,450 B2 | 2/2009 | Matusewicz et al. | |
| 7,489,403 B1 | 2/2009 | Lin et al. | |
| 7,553,453 B2 | 6/2009 | Gu et al. | |
| 7,616,315 B2 | 11/2009 | Sharrock et al. | |
| 7,651,851 B2 | 1/2010 | Clarke et al. | |
| 7,682,801 B2 | 3/2010 | Esfandiari | |
| 7,688,440 B2 | 3/2010 | Clarke et al. | |
| 7,740,801 B2 | 6/2010 | Saini et al. | |
| 7,763,454 B2 | 7/2010 | Nazareth et al. | |
| 7,803,322 B2 | 9/2010 | Barich et al. | |
| 7,815,854 B2 | 10/2010 | Cohen | |
| 7,879,597 B2 | 2/2011 | Esfandiari | |
| 7,879,624 B2 | 2/2011 | Sharrock | |
| 7,927,561 B2 | 4/2011 | Kirakossian et al. | |
| 7,941,376 B2 | 5/2011 | Peckover | |
| 8,003,060 B2 | 8/2011 | Cracauer et al. | |
| 8,018,593 B2 | 9/2011 | Tan et al. | |
| 8,030,091 B2 | 10/2011 | Jerome et al. | |
| 8,040,494 B2 | 10/2011 | Ermantraut et al. | |
| 8,093,057 B2 | 1/2012 | Choi et al. | |
| 8,101,431 B2 | 1/2012 | McDevitt et al. | |
| 8,105,552 B2 | 1/2012 | Xiao et al. | |
| 8,105,794 B2 | 1/2012 | Shaari | |
| 8,105,849 B2 | 1/2012 | McDevitt et al. | |
| 8,110,392 B2 | 2/2012 | Battrel et al. | |
| 8,128,871 B2 | 3/2012 | Petruno et al. | |
| 8,133,671 B2 | 3/2012 | Williams et al. | |
| 2001/0021536 A1 | 9/2001 | Lee | |
| 2002/0004246 A1 | 1/2002 | Daniels et al. | |
| 2002/0031839 A1 | 3/2002 | McNierney et al. | |
| 2002/0111741 A1 | 8/2002 | Abraham-Fuchs et al. | |
| 2003/0032199 A1 | 2/2003 | Meusel et al. | |
| 2003/0049175 A1 | 3/2003 | Buechler et al. | |
| 2003/0119030 A1 | 6/2003 | Zilber | |
| 2004/0019301 A1 | 1/2004 | Wong et al. | |
| 2004/0119591 A1 | 6/2004 | Peeters | |
| 2004/0151632 A1 | 8/2004 | Badley et al. | |
| 2005/0095697 A1 | 5/2005 | Bachur et al. | |
| 2005/0130120 A1 | 6/2005 | Lambotte et al. | |
| 2005/0136553 A1 | 6/2005 | Kaylor et al. | |
| 2005/0196318 A1 | 9/2005 | Matusewicz et al. | |
| 2005/0208593 A1 | 9/2005 | Vail et al. | |
| 2005/0221505 A1 | 10/2005 | Petruno et al. | |
| 2006/0019265 A1 | 1/2006 | Song et al. | |
| 2006/0019404 A1 | 1/2006 | Blatt et al. | |
| 2006/0025732 A1 | 2/2006 | Ying et al. | |
| 2006/0216832 A1 | 9/2006 | Nishikawa et al. | |
| 2006/0246513 A1 | 11/2006 | Bohannon | |
| 2006/0257992 A1 | 11/2006 | McDevitt et al. | |
| 2006/0263244 A1 | 11/2006 | Rannikko et al. | |
| 2007/0015285 A1 | 1/2007 | Catt et al. | |
| 2007/0020274 A1 | 1/2007 | Cole | |
| 2007/0031283 A1 | 2/2007 | Davis et al. | |
| 2007/0081920 A1 | 4/2007 | Murphy et al. | |
| 2007/0184495 A1 | 8/2007 | Shaari | |
| 2007/0231923 A1 | 10/2007 | Cumberland et al. | |
| 2007/0298436 A1 | 12/2007 | Lappe | |
| 2008/0102473 A1 | 5/2008 | Fouquet et al. | |
| 2008/0113391 A1 | 5/2008 | Gibbons et al. | |
| 2008/0113427 A1 | 5/2008 | Kikta | |
| 2008/0213920 A1 | 9/2008 | Nazareth et al. | |
| 2008/0311003 A1 | 12/2008 | Chiu | |
| 2009/0027501 A1 | 1/2009 | Elangovan et al. | |
| 2009/0035743 A1 | 2/2009 | Minter et al. | |
| 2009/0061507 A1 | 3/2009 | Ho | |
| 2009/0061534 A1 * | 3/2009 | Sharrock .......... G01N 21/8483 436/518 | |
| 2009/0155811 A1 | 6/2009 | Natan et al. | |
| 2009/0192820 A1 | 7/2009 | Bodlaender et al. | |
| 2009/0196792 A1 | 8/2009 | Raj et al. | |
| 2009/0197296 A1 | 8/2009 | Martin et al. | |
| 2009/0202388 A1 | 8/2009 | Matusewicz et al. | |
| 2009/0263905 A1 | 10/2009 | Scheuringer | |
| 2009/0280576 A1 | 11/2009 | Donati | |
| 2009/0298059 A1 | 12/2009 | Gumbrecht et al. | |
| 2009/0314946 A1 | 12/2009 | Song et al. | |
| 2010/0009430 A1 | 1/2010 | Wan et al. | |
| 2010/0055721 A1 | 3/2010 | Lambert et al. | |
| 2010/0087749 A1 | 4/2010 | Tovey | |
| 2010/0121156 A1 | 5/2010 | Yoo | |
| 2010/0135857 A1 | 6/2010 | Hunter et al. | |
| 2010/0176279 A1 | 7/2010 | Lai | |
| 2010/0239460 A1 | 9/2010 | Nazareth et al. | |
| 2010/0240149 A1 | 9/2010 | Nazareth et al. | |
| 2010/0248277 A1 | 9/2010 | Gibbons et al. | |
| 2010/0272635 A1 | 10/2010 | Rodems | |
| 2010/0291588 A1 | 11/2010 | McDevitt et al. | |
| 2010/0304397 A1 | 12/2010 | Burns et al. | |
| 2011/0038767 A1 | 2/2011 | Baril | |

(56) References Cited

U.S. PATENT DOCUMENTS

| | | |
|---|---|---|
| 2011/0151584 A1 | 6/2011 | Esfandiari |
| 2011/0178723 A1 | 7/2011 | Sharrock et al. |
| 2011/0195441 A1 | 8/2011 | Hemker et al. |
| 2011/0213564 A1 | 9/2011 | Henke |
| 2011/0213579 A1 | 9/2011 | Henke |
| 2011/0213619 A1 | 9/2011 | Henke |
| 2011/0266462 A1 | 11/2011 | Doi |
| 2011/0294199 A1 | 12/2011 | Bearinger et al. |
| 2012/0015448 A1 | 1/2012 | Sharrock |
| 2012/0096400 A1 | 4/2012 | Cho |
| 2012/0129272 A1 | 5/2012 | Petruno et al. |
| 2013/0065321 A1* | 3/2013 | Nazareth ............ G01N 21/8483 436/500 |
| 2013/0096400 A1 | 4/2013 | Dahl et al. |
| 2013/0280795 A1 | 10/2013 | Dahl et al. |
| 2014/0296667 A9 | 10/2014 | Dahl et al. |
| 2015/0094227 A1 | 4/2015 | McCarthy et al. |
| 2015/0204891 A1 | 7/2015 | Parsons |
| 2015/0241455 A1 | 8/2015 | Parsons |

FOREIGN PATENT DOCUMENTS

| | | |
|---|---|---|
| CN | 101137897 | 3/2008 |
| CN | 101551398 | 10/2009 |
| EP | 1051616 | 11/2000 |
| EP | 1484601 | 12/2004 |
| EP | 1918708 | 5/2008 |
| EP | 1718973 | 9/2009 |
| EP | 2385363 | 11/2011 |
| FR | 2929407 | 10/2009 |
| JP | H10-132817 | 5/1998 |
| JP | 2009085839 | 9/1999 |
| JP | H11-281645 | 10/1999 |
| JP | 2002510799 | 4/2002 |
| JP | 3496154 | 2/2004 |
| WO | WO 1995016207 | 6/1995 |
| WO | WO 1995033996 | 12/1995 |
| WO | WO 1996034287 | 10/1996 |
| WO | WO 1999006827 | 2/1999 |
| WO | WO 1999056111 | 11/1999 |
| WO | WO 2001098783 | 12/2001 |
| WO | WO 2002088739 | 11/2002 |
| WO | WO 2004003527 | 1/2004 |
| WO | WO 2005031355 | 4/2005 |
| WO | 2005059547 | 6/2005 |
| WO | WO 2005075982 | 8/2005 |
| WO | WO 2005084534 | 9/2005 |
| WO | WO 2005111579 | 11/2005 |
| WO | WO 2006091631 | 8/2006 |
| WO | WO 2006099191 | 9/2006 |
| WO | WO 2006119203 | 11/2006 |
| WO | WO 2006129761 | 12/2006 |
| WO | WO 2007049157 | 5/2007 |
| WO | WO 2006100415 | 9/2007 |
| WO | WO 2007132375 | 11/2007 |
| WO | WO 2007132376 | 11/2007 |
| WO | WO 2008001279 | 1/2008 |
| WO | WO 2010015843 | 2/2010 |
| WO | WO 2010055308 | 5/2010 |
| WO | WO 2010148252 | 12/2010 |
| WO | WO 2011091473 | 8/2011 |
| WO | WO 2011154918 | 12/2011 |
| WO | WO 2012010454 | 1/2012 |
| WO | WO 2012044530 | 4/2012 |
| WO | WO 2013036913 | 3/2013 |
| WO | 20014047692 | 4/2013 |
| WO | WO 2014085926 | 6/2014 |
| WO | 2015049508 | 4/2015 |
| WO | 2015121661 | 8/2015 |

OTHER PUBLICATIONS

Cole et al. (2009) "Background hCG in non-pregnant individuals: need for more sensitive point-of-care and over-the-counter pregnancy tests"; Clinical Biochemistry 42(3); pp. 168-175.

Cole et al. ( 2009) "Normal production of human chorionic gonadotropin in perimenopausal and menopausal women and after oophorectomy"; International Journal of Gynecological Cancer 19(9); pp. 1556-1559.

Cole et al. (2009) "Production of human chorionic gonadotropin during the normal menstrual cycle"; The Journal of Reproductive Medicine 54(4); pp. 245-250.

Cook et al. "Printed Circuit Board Tracking with RFID: Speed Efficiency and Productivity Made Simple"; Texas Instruments RFID White Paper (Feb. 2008); 9 pages.

Corker et al (1976) "Hormonal patterns in conceptual cycles and early pregnancy"; British Journal of Obstetrics and Gynaecology 83(6); pp. 489-494.

Extended European Search Report for European Application No. 14783290.1 dated Sep. 15, 2016.

Gronowski et al (2008) "Use of serum FSH to identify perimenopausal women with pituitary hCG"; Clinical Chemistry 54(4); pp. 652-656.

International Search Report and Written Opinion for Application No. PCT/AU2011/000085 dated May 18, 2011 (7 Pages).

International Search Report and Written Opinion for PCT/AU2013/001115 dated Dec. 17, 2013 (14 pages).

Jia et al. (1993) "Luminescence Luteinizing Hormone/ Choriogonadotropin (LH/CG) Bioassay: Measurement of Serum Bioactive LH/CG during Early Pregnancy in Human and Macaque"; Biology of Reproduction, vol. 49, Issue 6; pp. 1310-1316.

Liu et al. (2007) "Disposable electrochemical immunosensor diagnosis device based on nanoparticle probe and immunochromatographic strip"; Anal Chem. 79(20); 7644-7653.

Mishell Jr. et al. (1974) "Hormone patterns in early human gestation"; Basic Life Sciences.4(PT. B):371-384.

Mishell Jr. et al. (1973) "Serum gonadotropin and steroid patterns in early human gestation"; American Journal of Obstetrics and Gynecology 117(5); pp. 631-642.

Patent Examination Report No. 2 for Australian Patent Application No. 2013204428 dated Jan. 20, 2016 (7 pgs.).

Rowe et al. (1999) "An array immunosensor for simultaneous detection of clinical analytes"; Anal Chem. 71(2); pp. 433-439.

Snyder et al (2005) "Diagnostic considerations in the measurement of human chorionic gonadotropin in aging women"; Clinical Chemistry 51(10); pp. 1830-1835.

"Understanding Your Ovulation Cycle Female Menstrual Cycle Step by Step"; The Fertility Realm online. Jul. 9 2012. http://www.thefertilityrealm.com/ovulation-cycle.html]. Internet Archive. [www.https://web.archive.org/.veb/20120709173120/http:www.thefertilityrealm.com/ovulation-cycle.html] Accessed Jan. 13, 2016. (4 pages).

Wide L.; "Early Diagnosis of Pregnancy"; The Lancet, vol. 294, Issue 7626; Oct. 25, 1969, pp. 863-864.

Young et al. (2003) "Development of an ultrarapid one-step fluorescence immunochromatographic assay system for the quantification of microcystins"; Environ. Sci. Technol. 37 (9); 1899-19904.

Nilsson et al. (2001) "Immunological characterization of human luteinizing hormone with special regard to a common genetic variant"; Journal of Endocrinology 168; pp. 107-116.

* cited by examiner

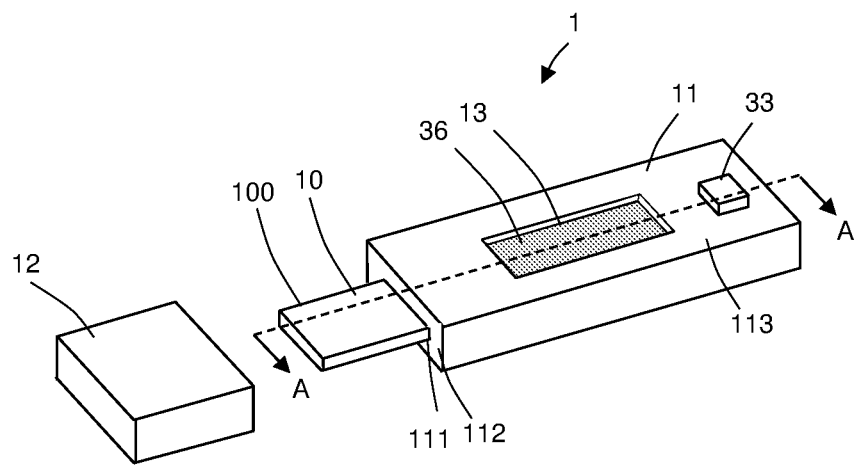
Fig. 1
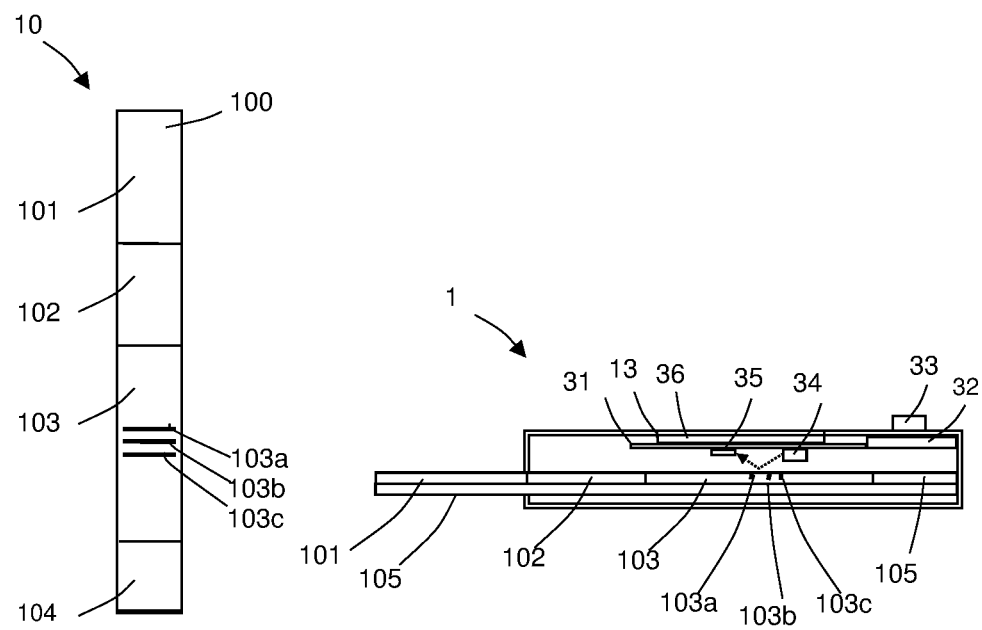
Fig. 2
Fig. 3

DIAGNOSTIC DEVICES AND METHODS FOR MITIGATING HOOK EFFECT AND USE THEREOF

CROSS-REFERENCE TO RELATED APPLICATION(S)

The present application claims priority from Australian provisional patent application no. 2015900186, the entire contents of which is incorporated herein by reference.

TECHNICAL FIELD

The present disclosure relates to devices and methods for identifying conditions in a human or animal body, such as pregnancy or ovulation. For example, the present disclosure relates to devices and methods for identifying pregnancy or ovulation, which devices and methods are adapted to mitigate the "hook effect", thereby improving accuracy of the devices and methods.

BACKGROUND

There exist many types of diagnostic devices for identifying target medical conditions in a human or animal. Increasingly, these devices are being designed for home use. The devices analyse a biological sample from the human or animal, such as a urine sample, blood sample or otherwise, and identify an analyte in the sample that provides a marker for a target condition.

One of the most widely used and recognised diagnostic devices is the home pregnancy test, which commonly employs lateral flow technology and uses human chorionic gonadotropin (hCG) as a marker for pregnancy.

Diagnostic devices that allow highly accurate testing are clearly desirable. Many diagnostic devices provide for binary identification of the target condition, where it is determined only if the target condition is present (a positive result) or not present (a negative result). In these devices, accuracy is a function of the sensitivity of the device, which is its ability to detect true positive results, and the specificity of the device, which is its ability to detect true negative results. Increasing accuracy is particularly important for diagnostic devices used at home, where there can be no trained health professional to interpret identification results and the value of the results to the care of a patient. The sensitivity of diagnostic devices increases when the devices are configured to detect smaller amounts of the marker analyte, yielding more true positive results. The sensitivity of a diagnostic device is particularly important to enable detection of early stage pregnancy when hCG may be present in serum or urine at low levels e.g., 1-20 IU/L. However, because the normal range of hCG in a pregnant woman can be from 1-200,000 IU/L, it is equally necessary for the accuracy of a diagnostic device to be able to detect hCG when present at higher levels.

A common problem which limits the accuracy of existing diagnostic devices for pregnancy is the dynamic range for detecting hCG, and in particular, the "hook effect" or "prozone effect" when hCG is present in a test sample at high levels. This is particularly common in diagnostic devices which employ sandwich assays when hCG is present in a test sample in sufficiently high concentrations to cause saturation (to a certain extent) of both the capture and signal (labelled) antibodies, thereby preventing the formation of a "sandwich". As a result, the signal generated is less than what would be expected at that concentration, and this results in detection of artificially low hCG or possibly even false negative results, when in fact hCG is present in a sample at high concentrations. Accordingly, there is a need to improve the dynamic range of diagnostic devices and assays which detect hCG to mitigate spurious results caused by the "hook effect".

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

As discussed above, hCG is a hormone produced during pregnancy and therefore measurement of the levels of hCG in a biological sample e.g., blood or urine, is a well-known procedure for testing pregnancy in women. Whilst it is important for a test apparatus or method to be relatively sensitive to low levels of hCG in order to detect pregnancy shortly after conception, the levels of hCG rapidly increase after conception. Accordingly, there is also a need to be able to detect hCG at high levels in order to accurately determine whether a woman is pregnant or not.

The present disclosure is based, in part, on the recognition that commercially available pregnancy tests can be inaccurate when hCG is present at high levels owing to the hook or prozone effect (referred to hereinafter only as "the hook effect"). For example, many commercially available pregnancy tests fail to provide an accurate quantitative (or semi-quantitative) measurement of hCG when high levels of hCG are present in a sample. The present disclosure provides devices and methods for detecting pregnancy in a subject which can extend the upper limit of the dynamic range for detecting hCG in a sample, thereby permitting the measurement of samples containing high levels of hCG that might otherwise appear to be low or non-existent owing to the hook effect. The devices and methods disclosed herein can also allow a more accurate quantitation of the level of hCG in a sample, at higher levels of hCG. This has many advantages, including the ability of the devices and methods disclosed herein to optionally indicate time since conception. Furthermore, by selecting appropriate capture reagents, the devices and methods disclosed herein can also be used simultaneously to determine whether a subject is pregnant or ovulating. In this regard, the present disclosure provides, for example, devices and methods which can mitigate the hook effect when detecting hCG in samples with high concentrations of hCG and which can serve the dual purpose of (i) determining whether or not a subject is pregnant, and (ii) determining whether or not a subject is ovulating.

In one aspect, the present disclosure provides an apparatus for detecting pregnancy and/or ovulation in a subject, said apparatus comprising one or more lateral flow test strips comprising:

(a) a label-holding portion comprising:
  (i) a first mobilisable capture reagent comprising a detectable label, wherein the first mobilisable capture reagent is configured to bind to human chorionic gonadotropin (hCG) to form a first complex; and
  (ii) a second mobilisable capture reagent comprising a detectable label, wherein the second mobilisable capture reagent is configured to bind to Luteinizing Hormone (LH) to form a second complex;

(b) a first test portion comprising an immobilised capture reagent configured to specifically bind hCG and thereby immobilise hCG to the first test portion; and
(c) a second test portion comprising an immobilised capture reagent configured to bind to both hCG and LH and thereby immobilise hCG and/or LH to the second test portion.

The detectable labels of the first and second capture reagents may be the same or may be different.

The one or more lateral flow test strips may be configured such that the second test portion is positioned downstream of the first test portion, and the first test portion is position downstream of the label-holding portion. Alternative configurations are described herein.

The immobilised capture reagent of the second test portion binds hCG with a lower affinity than the immobilised capture reagent of the first test portion. In other words, the immobilised capture reagent of the first test portion has a greater affinity for binding hCG than the immobilised capture reagent of the second test portion has for binding hCG.

In use, the apparatus can detect the presence or absence of hCG and/or LH in a biological sample obtained from a subject. The apparatus can also detect the presence of hCG in a sample when the level of hCG is high without "hooking out", thereby permitting an accurate determination of whether or not a woman from which the sample is obtained is pregnant or not. In particular, the apparatus can allow the accurate quantitation (or semi-quantitation) of the level of hCG in a sample when the sample contains high levels of hCG.

The ability to mitigate or reduce the hook effect and detect hCG at high levels can be achieved by virtue of the immobilised capture reagent at the second test portion having a lower binding affinity for binding hCG relative to the immobilised capture reagent at the first test portion. In this regard, if, during use, hCG is present in a sample in sufficiently high concentrations to cause saturation (to a certain extent) of both the mobilisable capture reagent for hCG and the immobilised capture reagent for hCG at the first test portion, then the formation of a sandwich between the labelled hCG complex and the immobilised capture reagent at the first test portion is prevented or significantly reduced. As a result, the signal generated at the first test portion does not provide an accurate indication of the true level of hCG in the sample. Thus, the signal at the first test portion may be low at low levels of hCG in the sample, and may be low at high levels of hCG in the sample. Indeed, it is possible that the signal may even be absent at the first test portion, despite the sample containing a high level of hCG.

However, in the apparatus disclosed herein, the labelled hCG complex in the sample is also able to bind the immobilised capture reagent at the second test portion, which has a lower affinity for hCG than the immobilised capture reagent at the first test portion. The lower binding affinity for binding hCG of the immobilised capture reagent at the second test portion, coupled with the configuration of the first and second test portions on the test strip, can therefore extend the upper limit of the dynamic range for detecting hCG in a sample. Thus, a "hook effect" should not be observed at the second test portion.

Furthermore, because the immobilised capture reagent at the second test portion may also bind LH, the apparatus of the disclosure can also be used to detect the presence or absence of LH in a sample and thereby determine if the woman from which the sample is obtained is ovulating.

The capture reagent of the first and/or second test portions may be an antibody. For example, the immobilised capture reagent of the first test portion may be an antibody configured to bind an epitope of hCG which is specific to hCG i.e., not present in LH. Thus, the antibody may not be cross-reactive with LH. The immobilised capture reagent of the second test portion may be an antibody which binds an epitope or region which is common to hCG and LH. For example, the immobilised capture reagent of the second test portion may be an anti-LH antibody capable of binding hCG.

The first and second mobilisable capture reagents of the label-holding portion may be conjugated to one or more detectable labels. The detectable labels may be the same or may be different. The labels may be conjugated directly to the mobilisable capture reagent, or may be conjugated to the mobilisable capture reagent via a linker. Any suitable detectable label known in the art may be used. The apparatus disclosed herein may comprise a control portion. The control portion may be positioned downstream of the second test portion. The control portion may comprise an immobilised or mobilisable reagent configured to detect a biological sample from a subject and/or configured to detect the first and/or second mobilisable capture reagent. Thus, the control portion may comprise an immobilised or mobilisable reagent configured to detect a biological sample from a subject e.g., urine or blood. Alternatively or in addition, the control portion may comprise an immobilised or mobilisable reagent configured to detect the first and/or second mobilisable capture reagent. The reagent configured to detect the first and/or second mobilisable capture reagent may be an antibody.

The one or more test strips of the apparatus of the disclosure may comprise a sample receiving portion configured to contact a biological sample from the subject e.g., urine or blood, or a component part of the sample. The sample receiving portion may be upstream of the label-holding portion of the test strip.

An apparatus in accordance with the present disclosure may also comprise a display, configured to present information about the identification of pregnancy and/or ovulation to a user.

The apparatus in accordance with the present disclosure may comprise a reader to identify hCG and/or LH. The reader may include one or more photodetectors capable of monitoring a light signal at the first and/or second test portions.

In general, the signals at the first and/or second test portions, which may be monitored or detected, may comprise light signals such as light reflection signals and/or fluorescent light signals or otherwise. The light signals may be generated as a result of detectable labels immobilised at the first and/or second test portions reflecting light and/or fluorescing light. The apparatus may comprise a light source that shines light on the first and/or second test portion to cause light reflection and/or fluorescing. Monitoring or detecting the presence and/or level of such light signals may comprise determining an absolute or relative intensity of the signals, for example. The absolute or relative intensity of the signals will be dependent on the number and type of detectable labels immobilised at the first and/or second test portions.

The apparatus of the present disclosure may be configured such that, in use:
(i) detection of a signal at the first test portion and not at the second test portion is indicative of pregnancy;
(ii) detection of a signal at the first test portion and at the second test portion is indicative of pregnancy;

(iii) detection of a signal at the second test portion and not at the first test portion is indicative of ovulation;

(iv) detection of no signal at the first or second test portions is indicative that the subject is not pregnant or ovulating.

The occurrence of a hook effect can be determined in (ii) above by a quantitative or semi-quantitative comparison of the signal at the first and second test portions. Such a comparison can also allow an accurate quantitation of the true level of hCG in the sample. This true level can be used, for example, to indicate the amount of time which has elapsed since conception.

For example, a low signal at the first test portion combined with a moderate or high signal at the second test portion may indicate a high level of hCG in the sample (and the occurrence of a hook effect). Alternatively, when the affinity of the immobilised capture reagent at the second test portion for hCG is lower than that at the first test portion, a low signal at the first test portion combined with a low signal at the second test portion may also indicate a high level of hCG in the sample (and the occurrence of a hook effect). It will be appreciated that the precise comparison of signals at the first and second test portions may depend on the particular affinities, quantities, and other properties of the immobilised capture reagents at the first and second test portions.

The occurrence of ovulation may be detected in (iii) above. Normally, this would occur when there are detectable levels of LH in the sample and undetectable levels of hCG in the sample. However, if some hCG is also present in the sample, some signal may also be detected at the first test portion. To avoid the possible misinterpretation of such a result as the occurrence of a hook effect, two different detectable labels can be used to distinguish LH from hCG at the second test portion. The use of two different detectable labels to distinguish LH from hCG at the second test portion may also safeguard against an incorrect interpretation of ovulation in the rare occurrence that there is so much hCG in the sample that there is no binding of hCG at the first test portion at all (an "extreme hook effect").

Alternatively or in addition, the apparatus may be configured to comprise a further, third test portion located downstream of the first and/or second test portion(s), wherein the third test portion comprises an immobilised capture reagent as in the first and/or second test portion(s). Detection and/or quantitation of a signal at the third test portion may provide an additional indication of the true level of hCG in the sample. It will be appreciated that the third test portion may be repeated one or more times (thereby introducing fourth, fifth, sixth etc. test portions each comprising an immobilised capture reagent as in the first and/or second test portion(s)).

The present disclosure also provides a method of determining whether or not a subject is pregnant or ovulating, said method comprising:

(a) contacting an apparatus of the present disclosure with a biological sample from the subject;

(b) detecting the presence and/or level of human chorionic gonadotropin (hCG) or Luteinizing Hormone (LH) at the first and/or second test portion(s);

(c) determining if the subject is pregnant or ovulating, or not pregnant and not ovulating, based on the presence and/or level of hCG and/or LH at the first and/or second test portion(s).

As indicated, the presence and/or level of hCG and/or LH in the sample can be determined by determining the presence and/or level of signals at the first and/or second test portion(s). Thus, any discussion herein of the detection of the level and/or amount of hCG and/or LH is to be interpreted as encompassing the determination of the presence and/or level of the associated signal.

The detection of the presence and/or level of hCG and/or LH at the first and/or second test portion(s) may indicate pregnancy and/or ovulation as described herein.

Whilst the apparatus and methods disclosed herein can include an immobilised capture reagent at the second test portion which is capable of binding LH and hCG, it is recognised that a number of other capture reagents capable of binding hCG with a lower affinity than that of the immobilised capture reagent at the first test portion may be used (particularly, though not necessarily exclusively, when the apparatus is not intended to detect ovulation). Thus, the second test portion may comprise any capture reagent capable of binding hCG with a lower affinity than that of the capture reagent at the first test portion. This is based on the recognition that the ability to extend the upper limit of the dynamic range for detecting hCG can be achieved by virtue of the differential affinities of the respective immobilised capture reagents at the first and second test portions for hCG. For example, the extension of the upper limit of the dynamic range for detection of hCG can be achieved when the immobilised capture reagent at the second test portion has a lower binding affinity for binding hCG relative to the immobilised capture reagent at the first test portion.

Accordingly, the present disclosure also provides in one aspect an apparatus for detecting pregnancy in a subject, said apparatus comprising one or more lateral flow test strips comprising:

(a) a label-holding portion comprising a mobilisable capture reagent comprising a detectable label, wherein the mobilisable capture reagent is configured to bind to human chorionic gonadotropin (hCG) to form a complex; and (b) a first test portion comprising an immobilised capture reagent configured to specifically bind hCG and thereby immobilise hCG to the first test portion; and (c) a second test portion comprising an immobilised capture reagent configured to bind to hCG with a lower affinity than the immobilised capture reagent at the first test portion.

The one or more lateral flow test strips may be configured such that the second test portion is positioned downstream of the first test portion, and the first test portion is positioned downstream of the label-holding portion. This apparatus may incorporate any one or more features of any other apparatus disclosed herein, in any combination.

The present disclosure also provides a method of detecting a high level of hCG in a biological sample, said method comprising:

(a) contacting an apparatus disclosed herein with the biological sample; and (b) detecting the presence and/or level of hCG at the first and/or second test portion(s);

wherein detecting the presence and/or a level of hCG at the second test portion is indicative of a high level of hCG being present in the biological sample.

In accordance with any method of the present disclosure, detecting hCG at the second test portion may be indicative of a high level of hCG being present in the biological sample. For example, the high level may be greater than 200,000 mIU/ml. For example, the high level may be at least 300,000 mIU/ml, at least 400,000 mIU/ml, at least 500,000 mIU/ml, at least 600,000 mIU/ml, at least 700,000 mIU/ml, at least 800,000 mIU/ml, at least 900,000 mIU/ml, or at least 1,000,000 mIU/ml of hCG.

In addition to mitigating the "hook effect", the apparatus, test strip and method described herein provide a means for more accurately quantitating the amount of hCG in a sample, particularly when present at high concentrations. For example, this may be achieved by detecting the presence and/or level of hCG at the second test portion. The apparatus, test strip and method described herein therefore provide the advantage of extending the upper limit of the dynamic range for detecting and quantitating hCG. When a signal is detected at the second test portion, the presence and/or strength of that signal may be correlated and/or combined with the signal detected at the first test portion; any such co-interpretation permitting the concentration of hCG to be determined quantitatively (or semi-quantitatively) with increased accuracy relative to a test apparatus or method in which only the first test portion is used. This has the advantage of allowing a more accurate determination to be made of the time since implantation of the blastocyst, from which a correlation can be made to the time since conception. Thus, the device, test strip and method disclosed herein can be used to determine the time since conception in a pregnant subject. In addition, the apparatus, test strip and method disclosed herein allows a quantitative or semi-quantitative detection of hCG to be performed.

Furthermore, quantitative or semi-quantitative detection of hCG also gives an indication that hCG levels are increasing at an anticipated rate during pregnancy.

Accordingly, the present disclosure also provides a method of determining time since conception in a subject, said method comprising:
(a) contacting an apparatus of the present disclosure with a biological sample from the subject;
(b) detecting the level of human chorionic gonadotropin (hCG) at the first and/or second test portion(s); and
(c) determining the amount of time that has elapsed since conception based on the level of hCG at the first and/or second test portion(s).

As described herein, the level of hCG in the sample can be determined by determining the presence and/or level of signals at the first and/or second test portion(s). Where signal is present at both the first and second test portions, the level of hCG in the biological sample may be determined by co-interpretation of the combined signals. The concentration of hCG in the sample may be determined quantitatively (or semi-quantitatively). Any discussion herein of the detection of the level and/or amount of hCG is to be interpreted as encompassing the determination of the level of the associated signal.

Based on the level of hCG determined to be in the biological sample, time since conception may be determined in accordance with a level, or one or more ranges of levels, of hCG known to be correlated with specific gestation age. In one example, a biological sample determined as having a level of hCG in the range of 5-50 mIU/ml e.g., in the range of 25-50 mIU/ml, may indicate that up to 3 weeks has elapsed since conception. In one example, a biological sample determined as having a level of hCG in the range of 5-426 mIU/ml e.g., in the range of 50-426 mIU/ml, may indicate that up to 4 weeks has elapsed since conception. In one example, a biological sample determined as having a level of hCG in the range of 18-7340 mIU/ml e.g., in the range of 426-7340 mIU/ml, may indicate that up to 5 weeks has elapsed since conception. In one example, a biological sample determined as having a level of hCG in the range of 1,080-56,500 mIU/ml e.g., in the range of 7,340-56,500 mIU/ml, may indicate that up to 6 weeks has elapsed since conception. In one example, a biological sample determined as having a level of hCG in the range of 7,650-229,000 mIU/ml e.g., in the range of 56,500-229,000 mIU/ml, may indicate that up to 7-8 weeks has elapsed since conception. In one example, a biological sample determined as having a level of hCG in the range of 25,700-288,000 mIU/ml e.g., in the range of 229,000-288,000 mIU/ml, may indicate that up to 9-12 weeks has elapsed since conception. Thus, the apparatus, test strip and method disclosed herein can be used to determine whether up to 3 weeks, up to 4 weeks, up to 5 weeks, up to 6 weeks, up to 7-8 weeks, up to 9-12 weeks, or any other time has elapsed since conception occurred in a pregnant subject.

Whilst the foregoing disclosure is directed to an apparatus and methods for detecting hCG in a sample for the purpose to determining pregnancy, it is recognised that the configuration of the apparatus described herein can be modified to detect other analytes and thereby extend the upper limit of the dynamic range for detecting those other analytes in a sample. Such a modified form of the apparatus would mitigate or reduce inaccuracies in the detection of the analyte owing to the hook effect when the analyte is present in a sample at high levels.

Accordingly, it is envisaged that the apparatus and methods described herein may be modified to accommodate detection of other analytes. For example, in one aspect the present disclosure provides an apparatus for detecting the presence and/or a level of an analyte in a sample from a subject, said apparatus comprising one or more lateral flow test strips comprising:
(a) a label-holding portion comprising a mobilisable capture reagent comprising a detectable label, wherein the mobilisable capture reagent is configured to bind to the analyte to form a complex; and
(b) a first test portion comprising an immobilised capture reagent configured to specifically bind to the analyte to the first test portion; and
(c) a second test portion comprising an immobilised capture reagent configured to bind to the analyte with a lower affinity than the immobilised capture reagent at the first test portion.

The one or more lateral flow test strips may be configured such that the second test portion is positioned downstream of the first test portion, and the first test portion is position downstream of the label-holding portion.

The present disclosure also provides a method of detecting a high level of an analyte in a biological sample, said method comprising:
(a) contacting an apparatus of the disclosure with the biological sample; and
(b) detecting the presence and/or level of the analyte at the first and/or second test portion(s);
wherein the presence and/or a level of the analyte at the second test portion is indicative of a high level of the analyte being present in the biological sample.

An apparatus in accordance with any aspect disclosed herein may comprise a single test strip or multiple test strips, as required. Where multiple test strips are present, features of the apparatus as disclosed herein may be present in each test strip or may be distributed across multiple test strips. Where multiple test strips are present, those test strips may be configured in series or in parallel. When in parallel, each test strip may be the same or may be different. For example, features of the apparatus as disclosed herein may be distributed across multiple test strips in parallel. The apparatus disclosed herein may comprise two or more test strips in parallel, wherein one of the test strips may be a test strip of the apparatus disclosed herein and the other one or more test strips may be configured to detect the target analyte (e.g., hCG) using a competition assay e.g., as described in WO2005/059547.

The present disclosure also provides use of an apparatus according to one or more aspects disclosed herein to detect pregnancy and/or ovulation in a subject. For example, the apparatus may be used in accordance with a method disclosed herein.

The apparatus according to one or more aspects of the present disclosure may be provided in the form a kit. In one example, a kit may comprise an apparatus according to one or more aspects of the present disclosure and instructions for use.

The apparatus according to one or more aspects of the present disclosure may also be configured to detect early pregnancy in accordance with the Applicant's PCT Publication No. WO2014/047692, the contents of which is incorporated herein by reference, such as in the embodiment described at page 18, paragraph [0079] to page 22, paragraph [0092] of WO2014/047692.

The present disclosure also provides a method of producing the apparatus according to one or more aspects disclosed herein. The method may comprise assembling one or more test strips disclosed herein in any one or more configuration disclosed herein.

The present disclosure also provides one or more lateral flow test strips. For example, in one aspect, the present disclosure provides a lateral flow test strip comprising:
(a) a label-holding portion comprising:
　(i) a first mobilisable capture reagent comprising a detectable label, wherein the first mobilisable capture reagent is configured to bind to human chorionic gonadotropin (hCG) to form a first complex; and
　(ii) a second mobilisable capture reagent comprising a detectable label, wherein the second mobilisable capture reagent is configured to bind to Luteinizing Hormone (LH) to form a second complex;
(b) a first test portion comprising an immobilised capture reagent configured to specifically bind hCG and thereby immobilise hCG to the first test portion; and
(c) a second test portion comprising an immobilised capture reagent configured to bind to both hCG and LH and thereby immobilise hCG and/or LH to the second test portion.

In another aspect, the present disclosure provides a lateral flow test strip lateral comprising:
(a) a label-holding portion comprising a mobilisable capture reagent comprising a detectable label, wherein the mobilisable capture reagent is configured to bind to the analyte to form a complex; and
(b) a first test portion comprising an immobilised capture reagent configured to specifically bind to the analyte to the first test portion; and
(c) a second test portion comprising an immobilised capture reagent configured to bind to the analyte with a lower affinity than the immobilised capture reagent at the first test portion.

The lateral flow tests trips of the preceding two aspects may be as described in conjunction with the apparatus of the preceding aspects.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of example with reference to the accompanying drawings, in which:

FIG. 1 shows an oblique view of a test device according to a first embodiment of the present disclosure;

FIG. 2 shows a top view of a test strip used in the test device of FIG. 1;

FIG. 3 shows a cross-sectional view of the test device of FIG. 1 along line A-A of FIG. 1;

DETAILED DESCRIPTION

Figure 4:
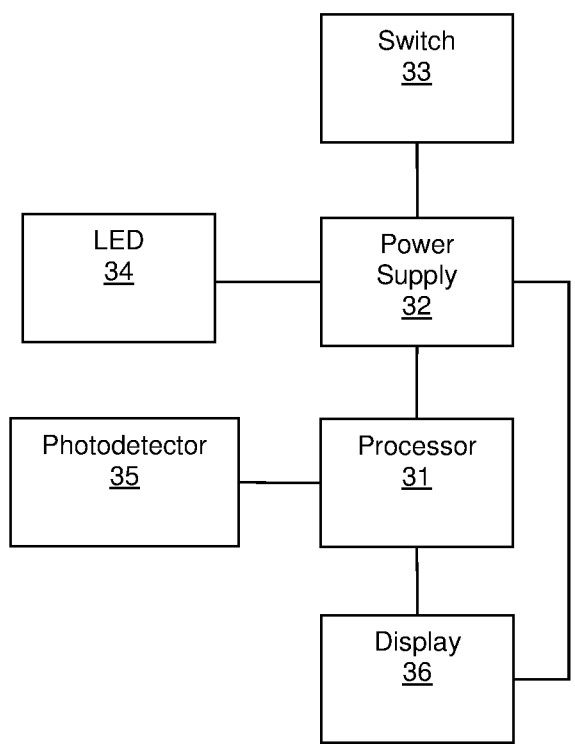
FIG. 4 shows a schematic representation of reading apparatus used in the test device of FIG. 1.

Tests configured to identify pregnancy based on a level of hCG in a sample typically do so using a hCG threshold level of 20 IU/L which is indicative of pregnancy. Moreover, in some tests, e.g. as disclosed in Applicant's PCT Publication No. WO2014/047692, identification of pregnancy using a hCG threshold level as low as 1 IU/L is disclosed. In general, such tests are therefore configured to detect hCG in biological samples at low levels, as may be the case in the early stages of pregnancy. However, the normal range of hCG in a pregnant woman can be from 1-200,000 IU/L or greater. In a small number of pregnancies, hCG levels can exceed 1,000,000 IU/L, for example. As discussed above, a common problem that limits the usefulness of traditional test devices for identifying pregnancy in biological samples in which hCG is present at high levels, is the phenomenon known as the "hook effect". The hook effect is a common phenomenon observed in the type of sandwich immunoassay traditionally used in pregnancy test devices when hCG is present in sufficiently high concentrations to cause saturation (to a certain extent) of both the capture and signal antibodies, thereby preventing formation of a "sandwich" as required to generate detectable signal or a signal that is indicative of the true level of hCG present in the sample. Accordingly, traditional pregnancy tests can detect artificially low levels of hCG, and even provide false negative results, when hCG is present in the urine sample at high concentrations.

To mitigate the "hook effect" and allow more accurate detection of pregnancy when hCG is present in high concentrations, the apparatus according to embodiments of the present disclosure is configured to have an increased dynamic range for detection of hCG.

Apparatus

The apparatus according to one or more embodiments of the present disclosure comprises one or more lateral flow test strips. Each lateral flow test strip may be formed of any material which permits flow of a liquid sample therethrough by capillary action and which is known to be suitable for use in lateral flow devices. Such materials have been widely used in commercially-available diagnostic tests e.g., pregnancy/conception tests, and will be known to a person skilled in the art. One such exemplary material may be a nitrocellulose membrane.

The one or more test strips may comprise a label-holding portion, a first test portion and a second test portion. The one or more test strips may also comprise a sample receiving portion and/or a control portion. The size of each of the label-holding portion, the first test portion, the second test portion, the sample receiving portion and the control portion may be adapted as necessary. For example, the precise dimensions of each may be adapted according to the particular dimensions of the one or more test strips used and/or the dimensions of the apparatus.

The apparatus may comprise more than one label-holding portion. Alternatively, or in addition, the apparatus may comprise more than one first test portion. Alternatively, or in addition, the apparatus may comprise more than one second test portion. Alternatively or in addition, the apparatus may comprise more than one control portion. Alternatively, or in addition, the apparatus may comprise more than one sample receiving portion.

The provision of more than one first test portion or more than one second test portion may further mitigate the hook effect and/or may allow a further quantitation of the hook effect. These additional test portions may be referred to as third, fourth, fifth, etc. test portions. Each of these additional test portions may comprise an immobilised capture reagent as is present in the first and/or second test portion(s). Preferably, each of these additional test portions comprises an immobilised capture reagent as is present in the second test portion.

The label-holding portion, the first test portion and the second test portion may be configured such that a biological sample taken from a subject contacts the label-holding portion before the first test portion, and such that the biological sample contacts the first test portion before the second test portion. The sample may contact the sample-receiving portion before the label-holding portion. The sample may contact the control portion after contacting the second test portion. Alternative configurations are possible, including configurations where multiple strips are present.

As used herein, the terms "downstream" and "upstream", when referring to the location of the various portions of the test strip, will be understood to mean relative to the direction of flow of the sample through or along the test strip.

The apparatus according to one or more embodiments of the present disclosure may also comprise a fluid sink, which may act to draw the sample through or along the one or more test strips.

The apparatus may comprise a single test strip, or multiple test strips. For example, an apparatus comprising multiple test strips may comprise 2, 3, 4, 5, 6, 7, 8, 9, 10, 15, 20 or more test strips. The test strips may be arranged in parallel or in a series.

As described herein, the lateral flow test strip of the apparatus may be configured to include one or more capture reagents. Capture reagents used in accordance with one or more embodiments of the present disclosure may be any one of more agents having the capacity to bind an analyte of interest in a sample. For example, the capture reagents may have the capacity to bind hCG specifically, or hCG and one or more of LH, FSH and TSH, as the case may be, to form a binding pair or complex. Some examples of such binding pairs or complexes include, but are not limited to, an antibody and an antigen (wherein the antigen may be, for example, a peptide sequence or a protein sequence); complementary nucleotide or peptide sequences; polymeric acids and bases; dyes and protein binders; peptides and protein binders; enzymes and cofactors, and ligand and receptor molecules, wherein the term receptor refers to any compound or composition capable of recognising a particular molecule configuration, such as an epitopic or determinant site.

The term "immobilised", as used with respect to a capture reagent, means the reagent is attached to the lateral flow test strip such that lateral flow of fluids through or along the test strip during an assay process will not dislodge the reagent. The capture reagent may be immobilised by any suitable means known in the art. Conversely, the terms "mobilisable" or "removable" is used to indicate that the capture reagent is capable of moving with the biological sample from the label-holding portion to the first and/or second test portion (s) and/or the control portion. The label may be deposited at the label-holding portion prior to use of the apparatus by any suitable means known in the art.

As used herein, the term "specifically binds", "binds specifically", "binds to specifically" or similar may refer to a capture reagent that does not bind significantly (e.g., above background binding levels) to any sample components other than the desired component or analyte. Accordingly, a capture reagent which "binds specifically to hCG" may not bind significantly or at all to any other analytes or components in a sample other than hCG, if hCG is in fact present.

The skilled person will be aware that an "antibody" is generally considered to be a protein that comprises a variable region made up of a plurality of immunoglobulin chains, e.g., a polypeptide comprising a $V_L$ and a polypeptide comprising a $V_H$. An antibody also generally comprises constant domains, some of which can be arranged into a constant region or constant fragment or fragment crystallizable (Fc). A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, human antibodies and chimeric antibodies. As used herein, the term "antibody" is also intended to include formats other than full-length, intact or whole antibody molecules, such as Fab, F(ab')2, and Fv which are capable of binding the epitopic determinant. These formats may be referred to as antibody "fragments". In accordance with one or more embodiments of the present disclosure, it will be expected that antibody fragments retain some or all of the ability of the corresponding full-length, intact or whole antibody to selectively bind to hCG, or to bind hCG and one or more of LH, FSH and TSH, as required, examples of which include, but are not limited to, the following:

(1) Fab, the fragment which contains a monovalent binding fragment of an antibody molecule and which can be produced by digestion of whole antibody with the enzyme papain to yield an intact light chain and a portion of one heavy chain;

(2) Fab', the fragment of an antibody molecule which can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab)2 is a dimer of two Fab' fragments held together by two disulfide bonds;

(4) Fv, defined as a genetically engineered fragment containing the variable region of the light chain and the variable region of the heavy chain expressed as two chains;

(5) Single chain antibody ("SCA"), defined as a genetically engineered molecule containing the variable region of the light chain, the variable region of the heavy chain, linked by a suitable polypeptide linker as a genetically fused single chain molecule; such single chain antibodies may be in the form of multimers such as diabodies, triabodies, and tetrabodies etc which may or may not be polyspecific (see, for example, WO 94/07921 and WO 98/44001); and (6) Single domain antibody, typically a variable heavy domain devoid of a light chain.

Accordingly, an antibody used as a capture reagent in accordance with one or more embodiments of the present disclosure may include separate heavy chains, light chains, Fab, Fab', F(ab')2, Fc, a variable light domain devoid of any heavy chain, a variable heavy domain devoid of a light chain and Fv. Such fragments can be produced by recombinant DNA techniques, or by enzymatic or chemical separation of intact immunoglobulins.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including a Fc region. The constant domains may be wild-type sequence constant domains (e.g., human wild-type sequence constant domains) or amino acid sequence variants thereof. In some cases, the intact antibody may have one or more effector functions.

An antibody used as a capture reagent in accordance with one or more embodiments of the present disclosure may be a humanized antibody. The term "humanized antibody", as used herein, refers to an antibody derived from a non-human antibody, typically murine, that retains or substantially retains the antigen-binding properties of the parent antibody but which is less immunogenic in humans.

The immobilised capture reagents of the first and/or second test portion(s) may be antibodies. For example, the immobilised capture reagent of the first test portion may be an antibody configured to bind an epitope specific to hCG. Preferably, an antibody thus configured will not be cross-reactive with other glycoprotein hormones having conserved regions, such as, for example, LH, FSH or TSH, if they are also present in a sample. For example, an antibody used as a capture reagent at the first test portion may be a monoclonal antibody against the β-subunit of hCG.

The immobilised capture reagent of the second test portion may be an antibody which binds an epitope or region which is common to hCG and one or more of LH, FSH and TSH. The immobilised capture reagent of the second test portion may be, for example, an anti-LH antibody capable of binding hCG, an anti-FSH antibody capable of binding hCG, or an anti-TSH antibody capable of binding hCG. In each case, it will be appreciated that the immobilised capture reagent of the second test portion will be configured to bind hCG with a lower affinity than the immobilised capture reagent of the first test portion.

Suitable antibodies for use in accordance with one or more embodiments of the present disclosure are commercially available or otherwise known in the art e.g., as disclosed in Nilsson et al., (2001) *Journal of Endocrinology*, 168:107-116. Furthermore, methods for determining the binding specificity and affinity of antibodies are known in the art, such that a skilled person could readily identify binding reagents which are suitable for use in accordance with one or more embodiments of the present disclosure.

As described herein, the label holding portion of the lateral flow test strip comprises at least one mobilisable capture reagent configured to bind hCG present in the sample. The mobilisable capture reagent may be conjugated to a detectable label to facilitate detection of hCG in the sample during use of the apparatus.

Where the apparatus is configured to detect and/or quantify a level of a further analyte capable of binding to the immobilised capture reagent of the second test portion e.g., LH or FSH, the label holding portion of the lateral flow test strip may comprise a second mobilisable capture reagent. The second mobilisable capture reagent may be configured to bind to that further analyte and may also be conjugated to a further or different detectable label to facilitate detection of the further analyte and differentiation from hCG. Such may be the case when the apparatus is configured for detecting pregnancy and/or ovulation in a subject.

Suitable detectable labels for use in diagnostic applications are known in the art. Suitable detectable labels for use in accordance with one or more embodiments of the present disclosure may include, for example, particulate labels, radiolabels, fluorescent labels, enzymatic labels and imaging agents. For example, the labels may comprise latex or gold. For example, the labels may be latex beads (of any colour, including of two or more distinguishable colours). The labels may also be nanoparticles. Any suitable nanoparticle may be used. The labels may be fluorescent labels e.g., a fluorescent molecule. Where the lateral flow test strip incorporates multiple fluorescent molecules, the respective molecules may be selected to fluoresce at different wavelengths e.g., upon excitation by light, to enable differential detection of two or more analytes in the sample (e.g., hCG and LH). The labels may be reflective. Where the lateral flow test strip incorporates multiple reflective molecules, the respective molecules may be selected to reflect light at different wavelengths to enable differential detection of two or more analytes in the sample (e.g., hCG and LH).

The mobilisable capture reagent(s) of the label-holding portion may be conjugated to detectable labels by any means known in the art. For example, the detectable label may be conjugated to the capture reagent via a suitable linker.

The apparatus in accordance with one or more embodiments of the present disclosure may be a device that operates as a single unit. For example, the apparatus may be provided in the form of a hand-held device. The apparatus may be a single-use, disposable, device. Alternatively, the apparatus may be partly or entirely re-usable. While in some embodiments the apparatus may be implemented in a laboratory, the apparatus may designed as a 'point-of-care' device, for home use or use in a clinic, etc. The apparatus may provide a rapid-test device, with identification of target conditions being provided to the user relatively quickly, e.g., in under 10 minutes, 5 minutes or under 1 minute The apparatus of one or more embodiments of the present disclosure may be configured for use with a variety of different types of biological samples. The sample may be a fluid sample. Biological samples which may be used in accordance with the apparatus and/or method of one or more embodiments of the present disclosure include, for example, blood, serum, plasma, urine, vaginal discharge and/or amniotic fluid. A preferred biological sample which may be used in accordance with the apparatus and/or method of one or more embodiments of the present disclosure is urine. Another preferred sample which may be used in accordance with the apparatus and/or method of one or more embodiments of the present disclosure is blood or component thereof e.g., serum or plasma.

Methods

The apparatus of one or more embodiments of the present disclosure may be used in a method of determining whether or not a subject is pregnant or ovulating. The methods may be carried out in a home environment or in a laboratory setting, or other environment. The methods may comprise using an apparatus of an embodiment as disclosed herein.

Kits

The apparatus of one or more embodiments of the present disclosure may be provided in the form a kit. In one example, a kit may comprise an apparatus of an embodiment of the present disclosure and instructions for use. The instructions for use may provide directions for using the apparatus to determine whether or not a subject is pregnant or ovulating in accordance with a method of one or more embodiment of the present disclosure. Alternatively, or in addition, a kit may comprise an apparatus of one or more embodiments of the present disclosure and one or more test strips compatible for use in the apparatus. In this respect, the apparatus may be configured to allow removal of a used test strip from the casing after use and subsequent placement with a new test strip into the casing.

Description of Exemplary Embodiments

Apparatus, and specifically a test device 1, according to an embodiment of the present disclosure, is illustrated in FIGS. 1 to 3. The test device 1 is a hand-held device and is configured to (i) detect pregnancy in a woman at least partially by identifying amounts (levels) of hCG hormone in a urine sample from the woman, (ii) identify if the woman is in the ovulation phase of a menstrual cycle at least partially by identifying amounts (levels) of LH hormone in the urine sample; or (iii) identify that the woman is neither pregnant nor ovulating at least partially based on the identified levels of hCG and LH in the urine sample.

The test device 1 includes an elongate lateral flow test strip 10 and a casing 11. The test strip 10 is partially housed in the casing 11 with a sampling end 100 of the test strip 10 protruding from an opening 111 in an end surface 112 of the casing 11, allowing urine sample to be received directly thereon. The sampling end 100 of the test strip 10 is coverable by a cap 12. The test device 1 also includes an LCD display 36 visible through an opening 13 in a top surface 113 of the casing 11 for displaying results of testing.

Referring to FIGS. 2 and 3, the test strip 10 is a lateral flow test strip including different zones arranged sequentially along the length of the strip, including a sample receiving zone 101 at the sampling end 100, a label-holding zone 102, a test zone 103, and a sink 104. The zones 101-104 comprise chemically-treated nitrocellulose, located on a waterproof substrate 105. The arrangement of the test zones 101-104 and substrate 105 is such that the urine sample, when directed onto the sample receiving zone 101, is absorbed into the sampling receiving zone 101 and at least part of the sample travels under capillary action sequentially through the sample receiving zone 101, the label-holding zone 102, and the test zone 103 and accumulates finally at the sink 104.

The label-holding zone 102 comprises three types of label-conjugated antibodies in this embodiment. The first label-conjugated antibody is designed to bind specifically to hCG, if present, in the urine sample to form a complex with the hCG (hereinafter "labelled hCG complex"). The second label-conjugated antibody is designed to bind specifically to luteinizing hormone (LH), if present, in the urine sample to form a complex with the LH (hereinafter "labelled LH complex"). Accordingly, as the urine sample travels through the label-holding zone 102, hCG present therein binds to the first label-conjugated antibody to form a labelled hCG complex and LH present therein binds to the second label-conjugated antibody to form a labelled LH complex. The third label-conjugated antibody is designed for use as a control. The sample containing the labelled hCG complex, labelled LH complex and/or the control label-conjugated antibody continues to travel though the test strip to the test zone 103 and contact a first test stripe 103a (or other type of test portion) that contains immobilized compounds capable of binding hCG, in particular hyperglycosylated hCG, with high specificity and affinity. In this regard, the immobilised compound may not exhibit any detectable cross-reactivity to LH. On contact, the immobilized compounds in the first test stripe 103a binds to the hCG in the labelled hCG complex to form a labelled hCG sandwich. The urine sample continues through the test strip and contacts a second test stripe 103b that contains immobilized reagents capable of independently binding to both hCG and LH. The immobilized reagents in the second test stripe 103b may have an affinity for binding to hCG that is lower than that of the immobilised reagents in the first test stripe 103a. If sufficient amount of labelled hCG complex is present in the sample, the immobilized reagents in the second test stripe 103b will bind to the hCG complex to form a labelled hCG sandwich. Equally, if sufficient amount of labelled LH complex is present in the sample, the immobilized reagents in the second test stripe 103b will bind to the LH complex to form a labelled LH sandwich. The urine sample will continue through the test zone to contact a control stripe 103c which contains immobilized reagents capable of binding the control label-conjugated antibody.

In this embodiment, the three label-conjugated antibodies are labelled with different types of fluorescent quantum dots (QDs), configured to fluoresce at a different specific emission peak wavelengths following UV light excitation (e.g., first, second and third wavelengths of 525, 625 and 800 nm, respectively). Of course, in alternative embodiments, other types of labels may be used in place of quantum dots, such as latex beads or gold particles, etc., and/or other specific emission peak wavelengths may be used.

In the present embodiment, by illuminating the stripes 103a, 103b, 103c with UV light, the presence of one or more of the different types of the QD labels will result in a detectable light emission with one or more different emission peak wavelengths. The intensity of the light emission (the size of the peaks) for the different wavelengths is indicative of the number of and type of labelled complexes/ antibodies bound to the stripes, which is in turn indicative of the prevalence of hCG and/or LH in the sample and the amount of the sample that has reached the control stripe. As such, one or more wavelength sensitive photodetectors, forming part of a reader, can be used in the test device 1 to identify the amounts of hCG and/or LH in the sample through monitoring of the test stripes 103*a* and 103*b*. The one or more photodetectors can also be used to determine, through monitoring of the control stripe 103*c*, that a sufficient amount of sample has travelled through the test stripes 103*a* and 103*b* to the control stripe 103*c* and that binding of the labelled complexes has been successful.

Referring to FIGS. 3 and 4, reading apparatus of the test device 1 of the present embodiment is now described in more detail. The reading apparatus includes a printed circuit board having a processor 31, a power supply (battery) 32, a switch 33, a UV LED 34, a multi-wavelength photodetector 35 and the display 36. The LED 34 is configured to emit light in the UV spectrum (at about 300 to 400 nm) that is incident on the stripes 103*a*, 103*b*, 103*c* to cause excitation of any quantum dot labels located thereon. The multi-wavelength photodetector 35 in combination with the processor 31 is configured to detect the different intensities of light emitted from the quantum dots at each of the three distinct wavelengths.

In use, the cap 12 is removed from sampling end 100 of the test strip and a urine sample is directed onto the sample receiving zone 101. The cap 12 can be replaced and, after approximately 1 or 2 minutes, giving sufficient time for the lateral flow process to take place, the switch 33 can be depressed, causing flow of electricity from the power supply 32 to the LED 34, resulting in emission of UV light from the LED 34 that is incident on the stripes 103*a*, 103*b*, 103*c* of the test strip 10. The UV light results in excitation of any or all of the different types of quantum dots that may be immobilized as part of the respective labelled complexes at the stripes 103*a*, 103*b*, 103*c*, causing light emission at respective wavelength peaks. In combination with the multi-wavelength photodetector 35, the processor 31 is configured to determine the size of the emission peaks and identify from this (a) if the sample mix has arrived at the control stripe 103*c* and labelling has been effective, and if yes, identify (b) an amount of hCG present in the sample based on the intensity of light emission detected at test stripe(s) 103*a* and/or 103*b*, or (c) an amount of LH present in the sample based on the intensity of light emission detected at test stripe 103*b*.

While a manual switch 33 is described above, in alternative embodiments, switching may be automated. For example, switching may be configured to occur upon replacement of the cap 12 onto the casing 11 or due to fluid activation, as the sample travels through a fluid-activated switch that may be provided in the device.

The LED may be carefully calibrated to ensure that the light emission from the LED is consistent from one device to the next, ensuring that a degree of excitation of the quantum dots is consistent. Additionally, or alternatively, a calibration mechanism may be integrated into the device. A known quantity of quantum dots, configured to fluoresce at yet another wavelength, may be immobilized on the test strip, e.g. at a further test stripe. Depending on the intensity of the fluorescence detected from the known quantity of quantum dots, the processor may adjust its interpretation of the light emission from quantum dots that label the LH and hCG analytes. Additionally, or alternatively, multiple LEDs may be used to excite the quantum dots with a view to suppressing the overall effect of any rogue LEDs.

If, during use, it is identified there is insufficient amount of sample to reach the control stripe, the processor 31 is configured to cause the display 36 to present the words INVALID TEST. In this respect, the processor 31, in combination with the multi-wavelength photodetector 35, is configured to determine the size of the emission peaks at the control stripe 103*c* and identify from this (i) if the sample has arrived at the control stripe 103*c*, and/or (ii) if labelling has been effective.

If, during use, it is identified there is sufficient amount of sample and labelling is effective, the processor 31 is configured to provide a determination of pregnancy or ovulation or neither.

Generally, the processor 31 is configured to: provide a determination of pregnancy if a signal above a threshold level is detected at the first test stripe 103*a*, but a signal above a threshold level is not detected at the second test stripe 103*b*; provide a determination of pregnancy if a signal above a threshold level is detected at the first test stripe 103*a* and a signal above a threshold level is detected at the second test stripe 103*b*; provide a determination of ovulation if a signal above a threshold level is not detected at the first test stripe 103*a*, but a signal above a threshold level is detected at the second test stripe 103*b*; and provide a determination of non-pregnancy and non-ovulation if a signal above a threshold level is not detected at the first test stripe 103*a* and a signal above a threshold level is not detected at the second test stripe 103*b*

The determination of ovulation as described above relies on there being no detectable level of signal at the first test stripe 103*a*. However, if some hCG is also present in the sample, some signal may also be detected at the first test stripe 103*a* even when the subject is ovulating. Through the use of QD labels configured to fluoresce at a different specific emission peak wavelengths, the device can distinguish between signal present at the second test stripe 103*b* that result from the presence of hCG or LH in the sample.

The device according to the present embodiment is configured to make a determination of a time since conception based on the levels of signals detected at the first and second test stripes 103*a*, 103*b* resulting from the presence of hCG in the sample. Greater levels of hCG in the sample can indicate a greater time since conception. The device can do this while mitigating the hook effect by interpreting the significance of low signal levels at the first test stripe 103*a* based on signal levels at the second test stripe 103*b*. The processor may be adapted to apply one or more algorithms to the detected signal levels to make this determination.

Figure 5:
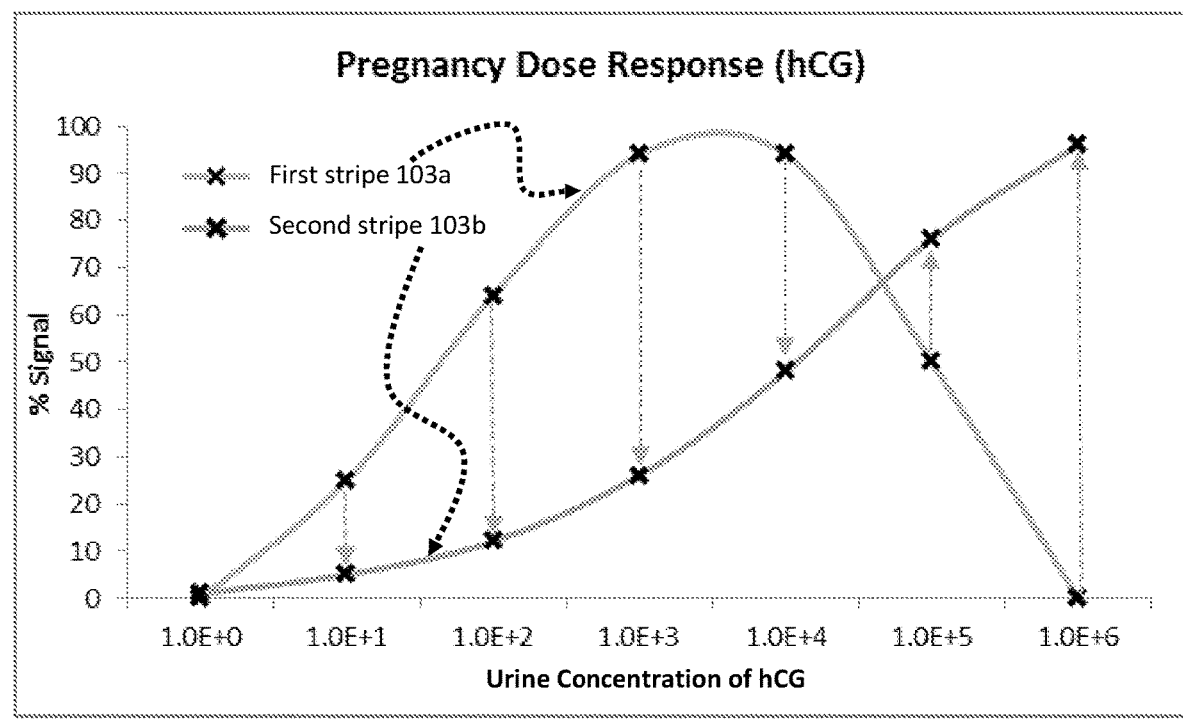
FIG. 5 shows a graph of example signal levels at first and second test portions of the device of FIG. 1 at varying concentrations of hCG in urine.

As can be seen in FIG. 5, changes in signal levels at the first and second test stripes 103*a*, 103*b* are not linearly correlated with the true levels of hCG in a test sample. The hook effect is evident at the first test stripe 103*a*, whereby the signal reduces at higher levels of hCG. The reduction is such that the same signal level can be present at both low and high levels of hCG. Nevertheless, the hook effect is not apparent at the second test stripe 103*b*. Accordingly, the signal level at the second test stripe 103*b* can be used to determine whether the signal level at the first test stripe 103*a* is indicative of a high or low true level of hCG in the sample. The processor according to the present embodiment may be programmed and adapted to co-interpret the signals at the first and second test stripes on this basis to predict the true level of hCG in the sample and therefore determine pregnancy and optionally a time since conception.

For example, where there are relatively low concentrations of hCG in the sample, with signal levels at a first wavelength and above a predetermined threshold being identified at the first test stripe 103*a* and not at the second test stripe 103*b*, the processor can determine the levels of hCG in the sample, and therefore pregnancy and optionally a time since conception, based entirely on the signal level identified at the first test stripe 103*a*. At these low level concentrations of hCG (e.g. towards the left side of the graph of FIG. 5), the hook effect has little impact on the signal level at the first test stripe 103*a*, and therefore a relatively accurate "high resolution" determination of low hCG levels can be made based on the signal level identified at the first test stripe 103*a*. On the other hand, where there are relatively high concentrations of hCG in the sample, with signal levels at the first wavelength and above a predetermined threshold being identified at the second test stripe 103*b*, the processor can determine the levels of hCG, and therefore pregnancy and optionally a time since conception, based entirely on the signal level identified at the second test stripe 103*b*. At these high level concentrations of hCG (e.g. towards the right side of the graph of FIG. 5), the hook effect has had a significant impact on the signal level at the first test stripe 103*a*. Nonetheless, a determination of high hCG levels can be made based on the signal level at the second test stripe 103*b*, which has not been affected by the hook effect. While the determination of hCG levels based on the second test stripe 103*b* may be "lower resolution" than those based on the first test stripe, since very high levels of hCG are being detected this can still allow a relatively accurate determination of a time since conception to be made, for example. Alternatively, a determination of hCG levels can be based on signal levels identified at both the first and second test stripes 103*a*, 103*b*.

Since the device of the present embodiment is a hand-held device, the device may be used at home, both while a woman is trying conceive (or contrarily as a contraceptive device), and also when they are pregnant. The device provides a combined ovulation prediction kit (OPK) and home pregnancy test (HPT).

The device is configured to allow removal of a used test strip from the casing 10, via the opening 111, and allow placement of a new test strip into the casing 10, via the same opening 111. Each time the strip is replaced, an identically configured test strip can be used, regardless of whether a woman is seeking to test for one or both of ovulation or pregnancy. In alternative embodiments, the device may be entirely a single-use device.

The device of this embodiment of the disclosure may also be configured to detect early pregnancy in accordance with the embodiment described at page 18, paragraph to page 22, paragraph [0092] of the Applicant's PCT Publication No. WO2014/047692.

In an alternative embodiment, the device may be substantially the same as described in the preceding embodiment, with the exception that the device is configured to detect hCG only in a sample.

The device of this alternative embodiment comprises only two types of label-conjugated antibodies. The first label-conjugated antibody is designed to bind specifically to hCG, if present, in the urine sample to form a complex with the hCG (hereinafter "labelled hCG complex"). The second label-conjugated antibody is designed for use as a control. Accordingly, as the urine sample travels through the label-holding zone, hCG present therein binds to the first label-conjugated antibody to form a labelled hCG complex. The sample containing the labelled hCG complex and the control label-conjugated antibody continues to travel though the test strip to the test zone and contact a first test stripe that contains immobilized reagents capable of binding hCG, in particular hyperglycosylated hCG, with high specificity and affinity. In this regard, the immobilised reagent does not exhibit any detectable cross-reactivity to LH and therefore does not detectably-bind LH, if present in sample. On contact, the immobilized reagents in the first test stripe bind to the hCG in the labelled hCG complex to form a labelled hCG sandwich. The urine sample will continue through the test strip and contact a second test stripe that contains immobilized reagents capable of binding independently to both hCG and LH. As in the first embodiment, the affinity for binding to hCG may be lower for the immobilised reagents in the second test stripe than the reagents contained in the first test stripe. If a sufficient amount of labelled hCG complex is present in the sample, the immobilized reagents in the second test stripe will bind to the hCG complex to form a labelled hCG sandwich. If any LH is present in the sample, the immobilized reagents in the second test stripe will bind the LH. However, LH will be in an unlabelled form and therefore non-detectable. The urine sample may then continue through the test zone to contact a control stripe which contains immobilized reagents capable of binding the control label-conjugated antibody.

The reading apparatus of the device of this embodiment is the same as that described in the previous embodiment with reference to FIGS. 3 and 4, such that, in use, the device according to this embodiment is able to identify pregnancy in the same way described for the first embodiment.

EXPERIMENTAL EXAMPLE 1

In this example, the inventors demonstrated the ability of an exemplary lateral flow test strip in accordance with the disclosure to detect hCG across a range of concentrations. The inventors demonstrated that a "hook effect" clearly occurs when hCG is present in a test sample at intermediate to high concentrations, and that a lateral flow test strip configured in accordance with the disclosure and described in this example can mitigate the "hook effect" thereby extending the dynamic range for detecting hCG.

Methods

Reagents used in this experiment were as follows:
  40 mm×300 mm nitrocellulose membrane having a capillary flow time of 120 seconds/4 cm;
  69.5 mm×300 mm Backing card;
  17 mm×300 mm Conjugate Release Pad;
  50 mm×300 mm Sample Pad;
  Phosphate buffered solution (PBS);
  50% maltose in PBS;
  Anti-hCG antibody, 1 mg/mL in PBS;
  Anti-LH antibody, 1 mg/mL in PBS;
  Goat anti-mouse antibody, 0.5 mg/mL in PBS;
  Anti-hCG 40 nm gold conjugate, 1 mL 10 OD; and
  hCG antigen.

Figure 6:
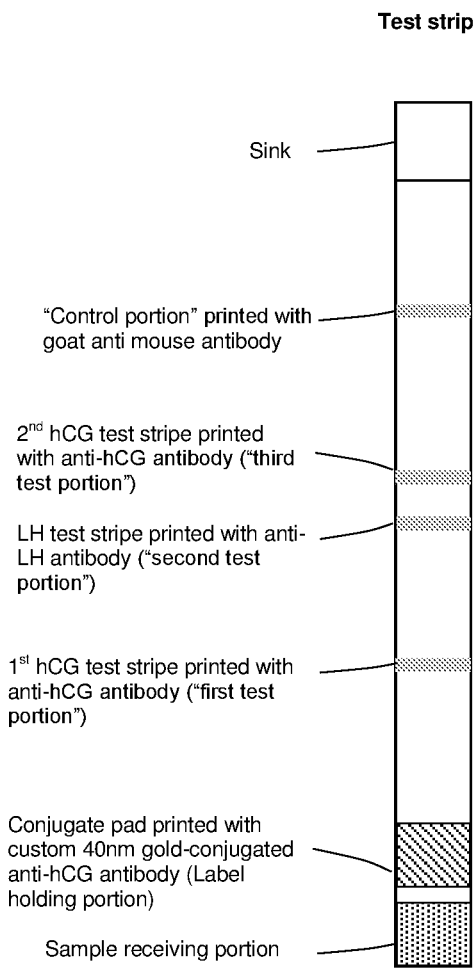
FIG. 6 shows a top view configuration of the test strip which was prepared and tested in the Experimental Example 1.

Briefly, test strips were prepared by laminating the 300 mm sections of nitrocellulose membrane, conjugate release pad (representing the "label holding portion) and sample pad (representing the "sample receiving portion") components onto an adhesive backing card using a standard laminator to achieve precise overlaps at the junctions of the three different materials. The assembled 300 mm cards were then slit into 4 mm wide test strips and configured in accordance with FIG. 6. Prior to assembly of the test strips, the nitrocellulose membrane component was prepared by printing three discrete capture lines using standard printing technology, with the anti-hCG antibody as a hCG capture at a position closest to the sample receiving portion (representing the "first test portion"), the anti-LH antibody downstream of the hCG capture (representing the "second test portion"), the anti-hCG antibody as a further hCG capture downstream of the LH capture (representing a "third test portion"), and the goat anti-mouse IgG control in the most downstream position (representing the "control portion"). Following assembly of the test strips, 40 mOD units of the anti-hCG gold conjugate (representing the "mobili sable capture reagent") was diluted in maltose and immobilised onto the conjugate release pad component and dried for 2 hours at 37° C.

Activity of the hCG antigen was confirmed as 12 492 IU/mg by the supplier using an ELISA. 1 mg of hCG antigen reconstituted in 2 ml PBS therefore produced a sample with 6,246,000 mIU/ml. Based on this activity, a series of test samples with varying concentrations of hCG were prepared by diluting the hCG antigen in PBS buffer according to the dilutions set out in Table 1.

TABLE 1

Test samples comprising varying concentrations of hCG

| Antigen #1 hCG | Final concentration mIU per mL |
|---|---|
| 1:2 | 3,123,000 |
| 1:5 | 1,249,200 |
| 1:10 | 624,600 |
| 1:50 | 124,920 |
| 1:100 | 62,460 |
| 1:500 | 12,492 |
| 1:1000 | 6,246 |
| 1:5000 | 1,249.2 |
| 1:10 000 | 624.6 |
| 1:50 000 | 124.9 |
| 1:100 000 | 62.5 |
| 1:500 000 | 12.5 |
| 1:1 000 000 | 6.25 |
| 1:2 000 000 | 3.15 |
| 1:5 000 000 | 1.25 |
| PBS | 0 |

For each test sample in the dilution series, 150 μl of test sample was added to the sample receiving portion of a separate test strip and the test strip was left to incubate at ambient temperature for 10 minutes (each dilution in the series was tested in replicates of five).

After the incubation period, the test strips were evaluated by visual inspection. The amount of light absorbed at the test and control capture zones was then quantified for each of the test strips using a TLC4 Scanner (CAMAG Scientific Inc.). A representative CAMAG scan is provided in FIG. 7.

Figure 8:
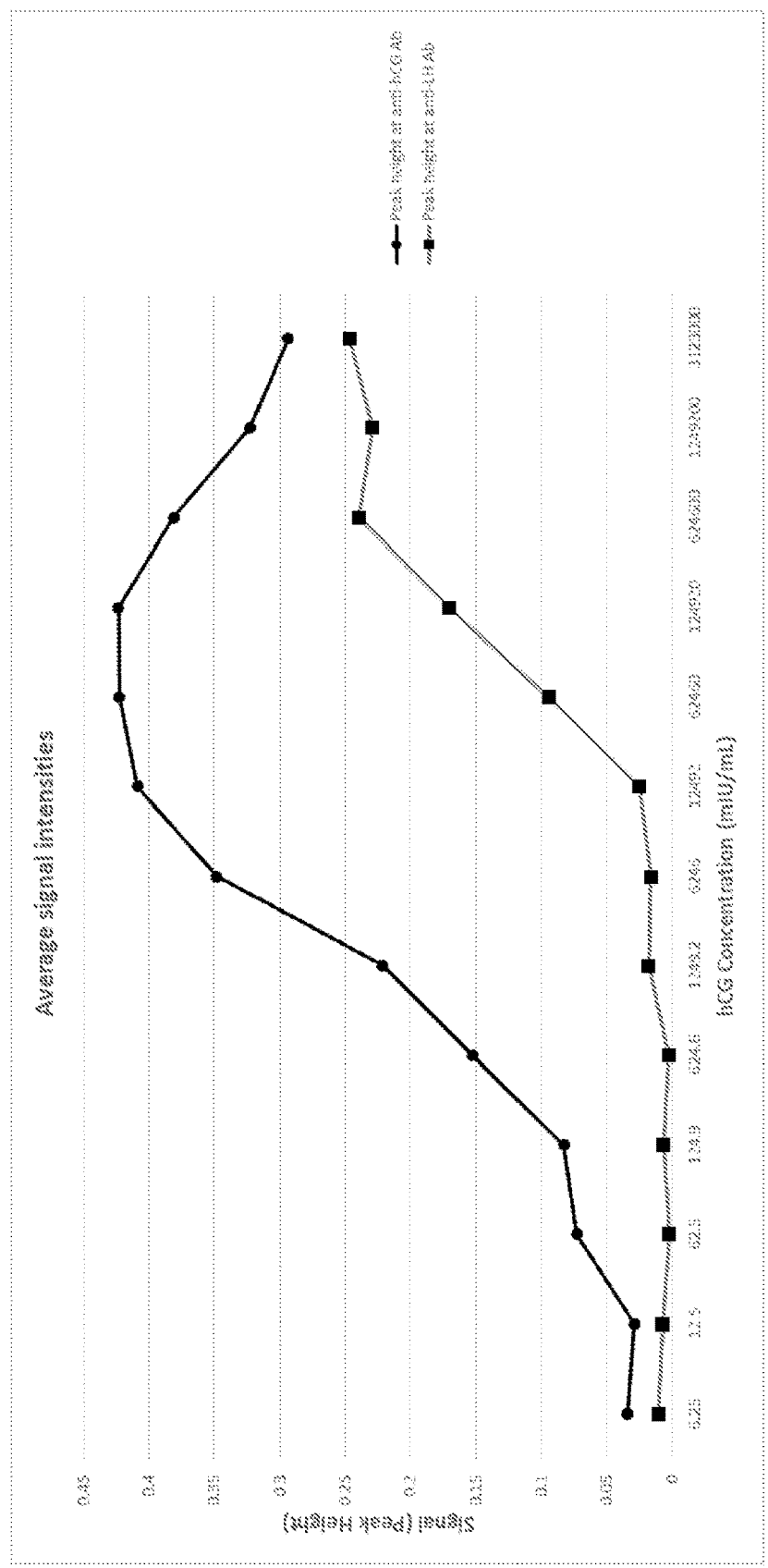
FIG. 8 is a graph plot showing the average signals detected by CAMAG Scan at the test portions printed with anti-hCG antibody and anti-LH antibody, respectively, for test strips incubated with test samples comprising concentrations of hCG across the dilution series described in Table 1.

Peak signal intensities at the anti-hCG and anti-LH capture zones were then plotted for each of the hCG antigen dilutions tested (FIG. 8).

Results

Figure 7:
FIG. 7 is a representative CAMAG Scan showing signal intensity at the test portions printed with anti-hCG antibody (peak series at approximately 0.95) and anti-LH antibody (peak series at approximately 0.6), respectively, for test strips incubated with test samples comprising concentrations of hCG across the dilution series described in Table 1. Dilutions 1:2 (left) to 1:1 000 000 (right). The CAMAG Scan illustrates the hook effect (plateauing of signal) at the test portion printed with anti-hCG antibody at the 1:5000 dilution coinciding with commencement and steady increase of signal at the test portion printed with anti-LH antibody.

As is apparent from FIGS. 7 and 8, an hCG hook effect was clearly observed at the first test portion printed with anti-hCG antibody i.e., the $1^{st}$ anti-hCG antibody. FIGS. 7 and 8 show that signal intensity at the first test portion increased as the hCG concentration of the test sample increased at low hCG concentrations (6.25 to 1249 mIU/ml; FIG. 7, lanes 13-8) before plateauing at intermediate hCG concentrations (6246 to 124,920 mIU/ml; FIG. 7, lanes 7-4) and then decreasing at high hCG concentrations (624,600 to 3,123,000 mIU/ml; FIG. 7, lanes 3-1). Furthermore, the hook effect observed at the first test portion was mirrored at the third test portion, which was also printed with the anti-hCG antibody, albeit observed with lower signal intensity. Whereas signal intensity at the second test portion printed with anti-LH antibody was absent or very low when the hCG concentration of the test sample was low (6.25 to 1249 mIU/ml; FIG. 7, lanes 13-8), steadily increased as hCG concentration reached intermediate concentrations (6246 to 124,920 mIU/ml; FIG. 8, lanes 7-4) before plateauing at high hCG concentrations (624,600 to 3,123,000 mIU/ml; FIG. 7, lanes 3-1). This trend was also apparent by visual inspection of the test strips.

As is apparent from FIGS. 7 and 8, the signal intensity at the second test portion printed with anti-LH antibody steadily increases for hCG concentrations which cause the signal intensity to plateau at the first test portion printed with anti-hCG antibody e.g., because the anti-hCG antibody becomes saturated. As such, the co-interpretation of signals detected at the first and second test portions makes it possible to extend the upper limit of the dynamic range for detecting hCG in a sample when present at high concentrations. The co-interpretation of signals also makes it possible to determine which side of the hook effect curve the signal is on, thereby more accurately determining the true hCG concentration in a test sample (semi-quantitatively or quantitatively). This may be particularly useful for accurately determining the amount of time which has elapsed since conception.

Whilst this experiment was performed using an anti-LH antibody as the capture reagent to bind hCG with a lower affinity than that of the anti-hCG antibody, it will be appreciated that other antibodies or binding proteins which are cross-reactive with hCG may be used (for example and without limitation, an anti-FSH antibody, anti-TSH antibody) as an alternative to the anti-LH antibody. Similarly, it will be apparent to skilled person that alternative configurations of the test strip in accordance with the disclosure herein may be employed.

The invention claimed is:

1. An apparatus for detecting pregnancy and/or ovulation in a subject, said apparatus comprising one or more lateral flow test strips comprising:
   (a) a label-holding portion comprising:
      (i) a first mobilisable capture reagent comprising a detectable label, wherein the first capture reagent is configured to bind to human chorionic gonadotropin (hCG) to form a first complex; and
      (ii) a second mobilisable capture reagent comprising a detectable label, wherein the second capture reagent is configured to bind to Luteinizing Hormone (LH) to form a second complex;
   (b) a first test portion comprising an immobilised capture reagent configured to specifically bind hCG and thereby immobilise hCG to the first test portion; and
   (c) a second test portion comprising an immobilised capture reagent configured to bind to both hCG and LH and thereby immobilise hCG and/or LH to the second test portion,
   wherein the immobilised capture reagent of the second test portion binds hCG with a lower affinity than the immobilised capture reagent of the first test portion.

2. The apparatus according to claim 1, wherein the detectable labels of the first and second capture reagents are the same.

3. The apparatus according to claim 1, wherein the detectable labels of the first and second capture reagents are different.

4. The apparatus according to claim 1, wherein the second test portion is positioned downstream of the first test portion, and the first test portion is positioned downstream of the label-holding portion.

5. The apparatus according to claim 1, wherein, in use, the apparatus detects the presence and/or level of hCG and/or LH in a biological sample of the subject.

6. The apparatus according to claim 1, wherein the immobilised capture reagents of the first and second test portions are antibodies.

7. The apparatus according to claim 6, wherein the immobilised capture reagent of the first test portion is an antibody configured to bind an epitope of hCG which is specific to hCG.

8. The apparatus according to claim 1, wherein the first and second mobilisable capture reagents of the label-holding portion are antibodies conjugated to detectable labels.

9. The apparatus according to claim 1, wherein the test strip comprises a control portion comprising an immobilised or mobilisable reagent configured to detect a biological sample from a subject and/or an immobilised or mobilisable reagent configured to detect the first and/or second mobilisable capture reagent(s).

10. The apparatus according to claim 1, wherein the test strip comprises a sample receiving portion configured to contact a biological sample from the subject.

11. The apparatus according to claim 1, comprising a display, wherein the apparatus is configured to present information about the identification of pregnancy and/and ovulation to a user via the display.

12. The apparatus according to claim 1, wherein the apparatus is provided in the form of a hand-held device.

13. The apparatus according to claim 1, comprising a reader to identify hCG and/or LH.

14. The apparatus of claim 13, wherein the reader includes one or more photodetectors capable of monitoring light reflection or light output at the first and second test portions.

15. A method of determining whether or not a subject is pregnant or ovulating, said method comprising:
  (a) contacting an apparatus of claim 1 with a biological sample from the subject;
  (b) detecting the presence and/or level of human chorionic gonadotropin (hCG) or Luteinizing Hormone (LH) at the first and/or second test portion(s); and
  (c) determining whether the subject is pregnant or ovulating based on the presence and/or level of hCG and/or LH at the first and/or second test portion(s).

16. The method according to claim 15, wherein:
  (i) detecting a signal at the first test portion and not at the second test portion is indicative of pregnancy;
  (ii) detecting a signal at the first test portion and second test portion is indicative of pregnancy;
  (iii) detecting a signal at the second test portion and not at the first test portion is indicative of ovulation; and
  (iv) detecting no signal at the first or second test portions is indicative that the subject is not pregnant or ovulating.

17. A method of detecting a high level of human chorionic gonadotropin (hCG) in a biological sample, said method comprising:
  (a) contacting an apparatus of claim 1 with the biological sample; and
  (b) detecting the presence and/or level of hCG at the first and/or second test portion(s);
  wherein detecting the presence and/or level of hCG at the second test portion is indicative of a high level of hCG being present in the biological sample.

* * * * *